US008311305B2

(12) United States Patent
Ohyu et al.

(10) Patent No.: US 8,311,305 B2
(45) Date of Patent: Nov. 13, 2012

(54) X-RAY DIAGNOSTIC APPARATUS, IMAGE PROCESSING APPARATUS, AND METHOD OF CALCULATING FILTER COEFFICIENTS USED FOR IMAGE FORMATION PROCESSING IN X-RAY DIAGNOSTIC APPARATUS AND THE LIKE

(75) Inventors: Shigeharu Ohyu, Yaita (JP); Masayuki Nishiki, Otawara (JP); Shingo Kanemitsu, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1071 days.

(21) Appl. No.: 11/869,330

(22) Filed: Oct. 9, 2007

(65) Prior Publication Data
US 2008/0095420 A1    Apr. 24, 2008

(30) Foreign Application Priority Data

Oct. 18, 2006    (JP) ................................. 2006-284325

(51) Int. Cl.
*G06K 9/00*    (2006.01)
*A61B 6/00*    (2006.01)
*G06K 9/40*    (2006.01)
(52) U.S. Cl. ...................................................... 382/131
(58) Field of Classification Search .......... 382/128–132, 382/260–265; 378/197, 205, 98.8
See application file for complete search history.

(56) References Cited

U.S. PATENT DOCUMENTS

| 4,740,896 | A | * | 4/1988 | Horiba et al. | ..................... 378/4 |
| 4,903,204 | A | | 2/1990 | Dobbins, III | |
| 6,196,715 | B1 | * | 3/2001 | Nambu et al. | ................. 378/197 |

FOREIGN PATENT DOCUMENTS

| JP | 2000-237182 | | 9/2000 |
| JP | 2004-313391 | * | 4/2003 |
| JP | 2005-021345 | * | 7/2003 |
| JP | 2004-73449 | | 3/2004 |
| JP | 2004-313391 | | 11/2004 |
| JP | 2005-13346 | | 1/2005 |

OTHER PUBLICATIONS

Japanese Office Action mailed May 15, 2012, in Japanese Patent Application No. 2007-269447 (with English Translation).
Japanese Office Action mailed on Aug. 21, 2012, in Japanese Patent Application No. 2007-269447 (with English Translation).

* cited by examiner

*Primary Examiner* — Vu Le
*Assistant Examiner* — Amara Abdi
(74) *Attorney, Agent, or Firm* — Oblon, Spivak, McClelland, Maier & Neustadt, L.L.P.

(57) ABSTRACT

A tomosynthesis image is generated by applying preprocessing to each image obtained by capturing a plurality of X-ray images at a plurality of X-ray tube positions and then performing filtering processing and backprojection. At this time, a proper filter coefficient used filtering is determined for each scan track, each image frame, and each pixel position in an image.

18 Claims, 9 Drawing Sheets

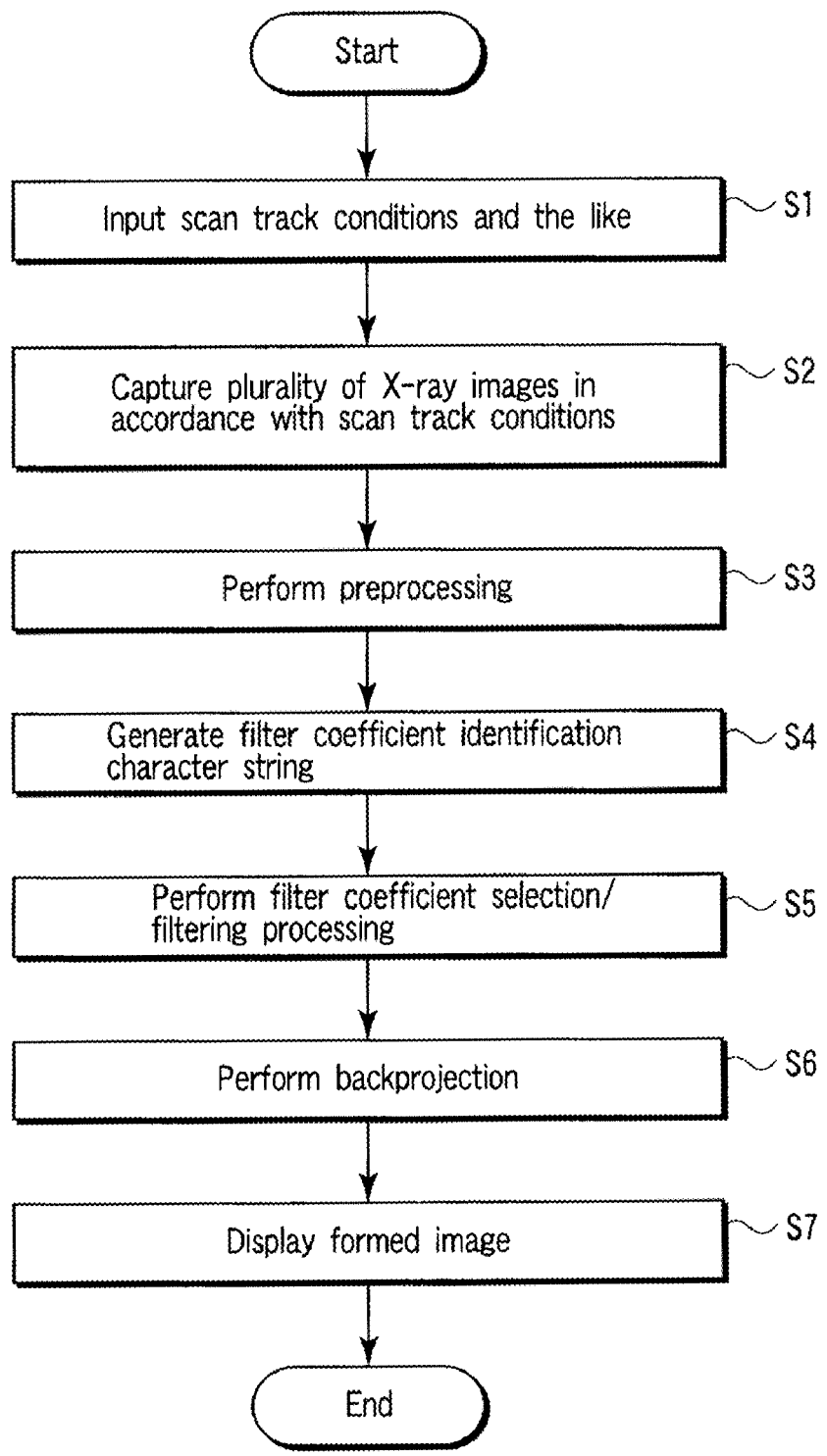
F I G. 12

X-RAY DIAGNOSTIC APPARATUS, IMAGE PROCESSING APPARATUS, AND METHOD OF CALCULATING FILTER COEFFICIENTS USED FOR IMAGE FORMATION PROCESSING IN X-RAY DIAGNOSTIC APPARATUS AND THE LIKE

CROSS-REFERENCE TO RELATED APPLICATIONS

This application is based upon and claims the benefit of priority from prior Japanese Patent Application No. 2006-284325, filed Oct. 18, 2006, the entire contents of which are incorporated herein by reference.

BACKGROUND OF THE INVENTION

1. Field of the Invention

The present invention relates to an image formation processing method used in the generation of X-ray tomosynthesis images.

2. Description of the Related Art

As image formation processing methods for digital tomosynthesis using an X-ray diagnostic apparatus or the like, there have been proposed various methods like James T Dobbins III, and Devon J Godfrey, "Digital X-ray tomosynthesis: current state of the art and clinical potential", Physics in Medicine and Biology Vol. 48, pp. R65-R106, 2003. As a representative technique, a technique called the filtered backprojection (FBP) method like that shown in FIG. 15 is available. The FBP method obtains multiple tomosyntheses by applying a filter to a plurality of images obtained by performing processing such as logarithmic computation for X-ray images captured from a plurality of directions, and performing backprojection for the images. As a filter to be used, for example, a filter called the Shepp-Logan filter (see the equation in FIG. 15) is known. The FBP method is characterized by applying the same filter coefficient to all X-ray images captured from many directions and applying the same filter to each image without changing the coefficient regardless of the position in one image. The filtered backprojection method is essentially a reconstruction method for a CT scanner which can perform perfect reconstruction, and is not an image formation processing method suitable for digital tomosynthesis incapable of perfect reconstruction. Owing to the characteristic that the processing time is short, however, there are many reports of research on the application of the filtered backprojection method to digital tomosynthesis.

In applying the filtered backprojection method to digital tomosynthesis, several image formation processing methods capable of obtaining high image quality have been proposed. For example, the result obtained by comparing an iterative image formation processing method called Maximum Likelihood algorithm (ML method) and the filtered backprojection method has been reported in Tao Wu, Richard H. Moore, Elizabeth A. Rafferty, and Daniel B. Kopans, "A comparison of reconstruction algorithms for breast tomosynthesis", Medical Physics, Vol. 31, No. 9, September 2004. This report indicates that the ML method is capable of obtaining better image quality than the filtered backprojection method, but the processing time in the ML method is three hr or more in contrast to the filtered backprojection method in which the processing time is 15 min or less. In addition, an image formation processing method called matrix inversion tomosynthesis disclosed in, for example, U.S. Pat. No. 4,903,204 is known. According to this technique, Ying Chen, Joseph Y. Lo, James T. Dobbins III, "Noise power spectrum analysis for several digital breast tomosynthesis reconstruction algorithms", Proc. SPIE vol. 6142, pp. 1677-1684, 2006 has reported that image quality higher than that obtained by the filtered backprojection method can be obtained.

In a clinical case, when X-ray tomosynthesis images are to be generated for examination, it is essential to provide image quality high enough to allow interpretation to detect the presence/absence or state of an abnormality. In practice, providing an examination image within a short processing time, e.g., several min, is as important as providing high image quality.

As described above, however, the conventional filtered backprojection method suffers from poor image quality, although the processing time is short. In addition, other image formation processing methods which provide high image quality take a long processing time, and hence are not good enough for practical use.

BRIEF SUMMARY OF THE INVENTION

The present invention has been made in consideration of the above situation, and has as its object to provide an X-ray diagnostic apparatus or image processing apparatus which can generate and display a tomosynthesis image with high image quality at high speed in digital tomosynthesis, and a method of calculating filter coefficients used for image formation processing in an X-ray diagnostic apparatus or the like.

According to an aspect of the invention, it is provided that an image processing apparatus comprises: a storage unit which stores an X-ray image for each frame which is acquired by applying X-rays to a subject to be examined while an X-ray tube is moved along a predetermined scan track and a different filter coefficient for each scan track, each frame of each X-ray image, and each pixel position of a detector; a filter processing unit which determines a filter coefficient for each pixel of each X-ray image on the basis of a combination of the predetermined scan track, the frame of the X-ray image, and the pixel position of the detector, and executes filter processing for an X-ray image or a processed image thereof for said each frame by using the determined filter coefficient; and a tomosynthesis image generating unit which generates a tomosynthesis image by using an X-ray image for said each frame after filter processing.

According to another aspect of the invention, it is provided that an X-ray diagnostic apparatus comprises: an imaging unit which applies X-rays to a subject to be examined while moving an X-ray tube along a predetermined scan track, and detects X-rays which enter a detection surface of a detector; an image generating unit which generates an X-ray image for each frame on the basis of the detected X-rays; a storage unit which stores a different filter coefficient for each scan track, each frame of an X-ray image, and each pixel position of the detector; a filter processing unit which determines a filter coefficient for each pixel of each X-ray on the basis of a combination of the predetermined scan track, the frame of the X-ray image, and the pixel position of the detector, and executes filter processing for an X-ray image or a processed image thereof for said each frame by using the determined filter coefficient; and a tomosynthesis image generating unit which generates a tomosynthesis image by using an X-ray image for said each frame after filter processing.

According to yet another aspect of the invention, it is provided that a method of calculating a filter coefficient used for reconstruction processing in digital tomosynthesis in an X-ray diagnostic apparatus, the method causing a computer to calculate an equivalent blurring function as a two-dimensional image for each combination of each scan track, each frame of an X-ray image, and each pixel position of the detector, calculate a deconvolution function of the equivalent blurring function, and calculate a filter coefficient for each combination of a scan track, a frame of an X-ray image, and a pixel position of the detector by using the deconvolution function.

According to yet another aspect of the invention, it is provided that a method of calculating a filter coefficient used for reconstruction processing in digital tomosynthesis in an X-ray diagnostic apparatus, the method causing a computer to calculate an equivalent blurring function by executing double integral with respect to backprojection, projection, backprojection, and projection, calculate a deconvolution function of the equivalent blurring function, and calculate a filter coefficient for each combination of a scan track, a frame of an X-ray image, and a pixel position on each X-ray image by using the deconvolution function.

BRIEF DESCRIPTION OF THE SEVERAL VIEWS OF THE DRAWING

FIG. 12 is a flowchart showing an operation procedure in image formation processing by the PI method in the mammography X-ray diagnostic apparatus 1;

DETAILED DESCRIPTION OF THE INVENTION

Figure 1:
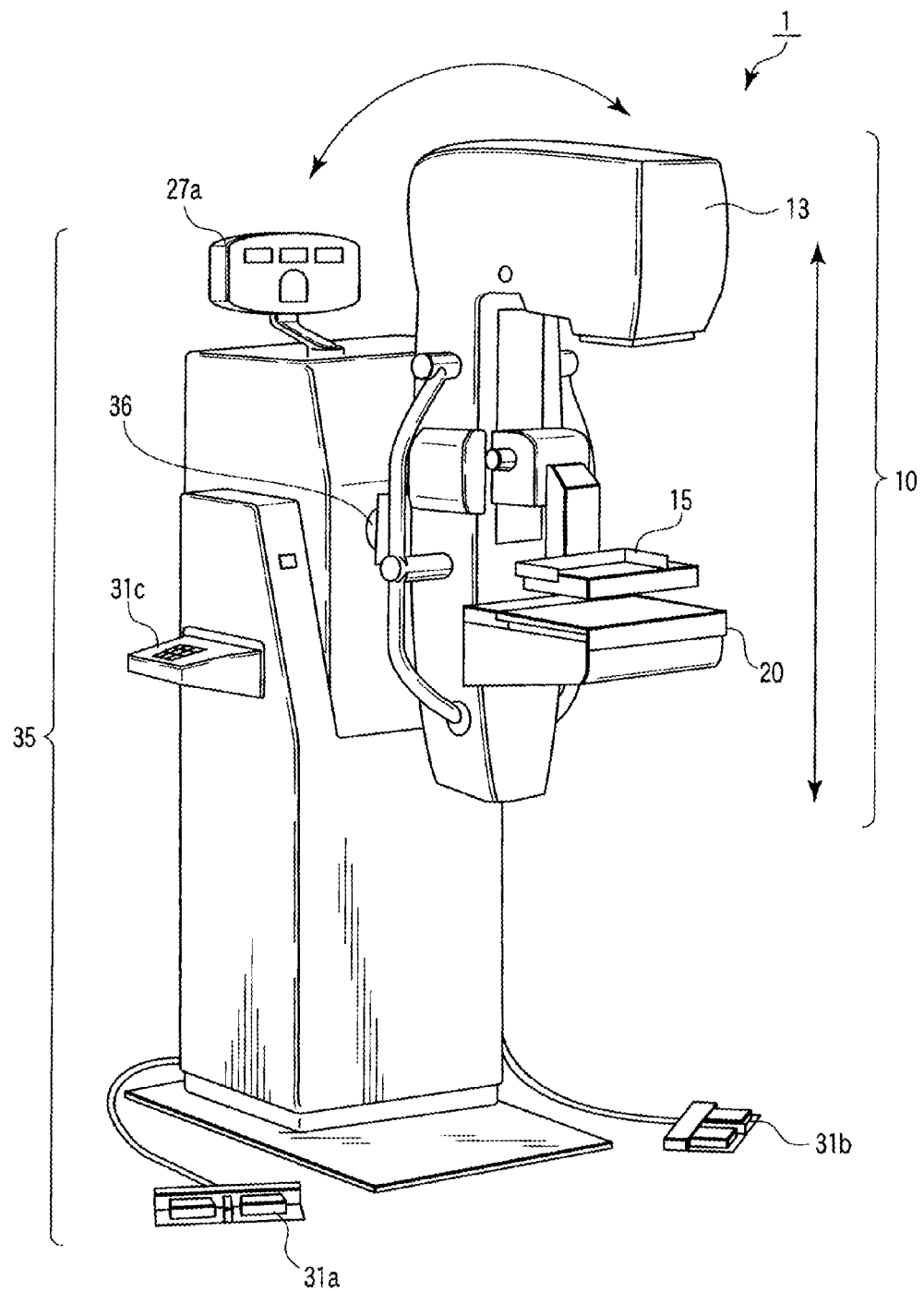
FIG. 1 is a perspective view of a mammography X-ray diagnostic apparatus 1 according to an embodiment.

An embodiment of the present invention will be described below with reference to the views of the accompanying drawing. Note that the same reference numerals denote constituent elements having substantially the same functions and arrangements, and a repetitive description will be made only when required.

Note that this embodiment will exemplify a case wherein the technical idea of the present invention is applied to a mammography X-ray diagnostic apparatus. However, the present invention is not limited to mammography and can be applied to any techniques which perform reconstruction processing such as digital tomosynthesis using X-rays (e.g., an X-ray diagnostic apparatus for circulatory imaging or the like).

FIG. 1 is a perspective view of a mammography X-ray diagnostic apparatus 1 according to this embodiment. As shown in FIG. 1, the mammography X-ray diagnostic apparatus 1 comprises an arm portion 10 and a support column 35. The arm portion 10 is provided with an X-ray source device 13, flat panel detector 20, compression paddle 15, and the like which face each other. The support column 35 is provided with a display panel 27a, foot pedals 31a and 31b, touch panel 31c, and the like. The arm portion 10 can move vertically with respect to the support column 35 and rotate/move about a shaft 36. Setting the arm portion 10 in a predetermined posture and fixing a breast between the detection surface of the flat panel detector 20 and the compression paddle 15 make it possible to acquire an image along a desired scan track when performing, for example, tomosynthesis.

Figure 2:
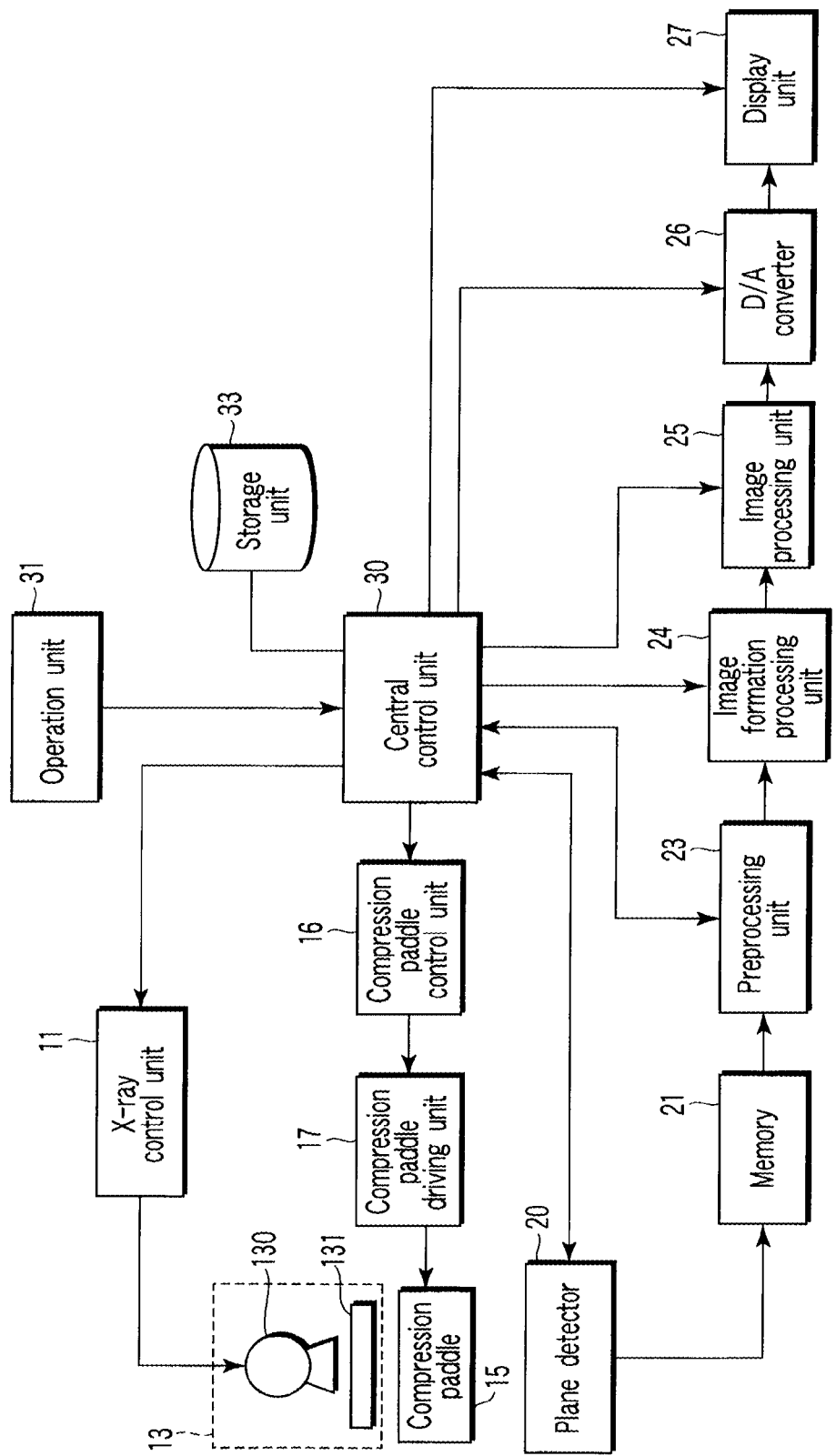
FIG. 2 is a block diagram of the mammography X-ray diagnostic apparatus 1 according to this embodiment.

FIG. 2 is a block diagram of the mammography X-ray diagnostic apparatus 1. As shown in FIG. 2, the mammography X-ray diagnostic apparatus 1 comprises an X-ray control unit 11, the X-ray source device 13, the compression paddle 15, a compression paddle control unit 16, a compression paddle driving unit 17, the flat panel detector 20, a memory 21, a preprocessing unit 23, an image formation processing unit 24, an image processing unit 25, a D/A converter 26, a display unit 27, a central control unit 30, an operation unit 31, and a storage unit 33.

The X-ray control unit 11 controls the X-ray source device 13 to apply X-rays with a predetermined intensity at a predetermined rate in accordance with an instruction from the central control unit 30.

The X-ray source device 13 includes an X-ray tube 130 and an X-ray field limiting device 131. The X-ray tube 130 is a vacuum tube which generates X-rays. The X-ray tube 130 generates X-rays by accelerating electrons by a high voltage from a high voltage generator and impinging a target with the electrons. The X-ray field limiting device 131 forms X-rays applied from the X-ray tube 130 into a predetermined shape.

The compression paddle 15 is used to compress the breast with the detection surface of the flat panel detector 20 so as to fix the breast while reducing its thickness at the time of imaging. Compressing and fixing (positioning) the breast in this manner can reduce scattered X-rays from the object and the overlap of mammary gland tissues, thereby, for example, improving image contrast, preventing the occurrence of noise due to body movement, and reducing the irradiation dose.

The compression paddle control unit 16 controls the compression paddle driving unit 17 to position the compression paddle 15 in accordance with an instruction from the central control unit 30. The compression paddle control unit 16 measures the compression thickness of the fixed breast (the thickness of the breast when it is compressed) and sends out the measured data to the central control unit 30.

The compression paddle driving unit 17 drives the compression paddle 15 under the control of the compression paddle control unit 16.

The flat panel detector 20 includes a scintillator and a photodiode array. The flat panel detector 20 generates electron holes by causing X-rays transmitted through an object to strike a photoelectric film, stores the electron holes in a semiconductor switch, and reads them as an electrical signal, thereby converting the X-rays into the electrical signal and detecting it. Note that this detector may use, as a conversion scheme, a direct conversion scheme of converting X-rays into an electrical signal or an indirect conversion scheme of converting X-rays into an electrical signal through light.

The memory 21 temporarily stores a digital signal supplied from the flat panel detector 20.

The preprocessing unit 23 generates a digital X-ray image by reading out a digital signal from the memory 21 for each frame and executes preprocessing (e.g., offset correction processing, blood vessel pixel correction processing, and logarithmic computation processing). Note that in this preprocessing, the preprocessing unit 23 may perform pixel bundling processing as needed.

The image formation processing unit 24 executes image formation processing by the projection inversion method (to be described later) under the control of the central control unit 30.

The image processing unit 25 performs predetermined image processing such as subtraction processing as needed by using an X-ray image for each frame.

The D/A converter 26 converts the digital signal string of the image data input from the preprocessing unit 23 into an analog signal string.

The display unit 27 includes a CRT, plasma display, liquid crystal display, or the like which displays an X-ray image such as a digital tomosynthesis image obtained from a signal received from the D/A converter 26 by tomosynthesis and a display panel 27a which displays the operation state of the apparatus. The display unit 27 displays a window for inputting conditions concerning a scan track in image formation processing by the projection inversion method to be described later.

The central control unit 30 is a central processing unit which performs control concerning the acquisition of image data, image processing of the acquired image data, and control concerning image playback processing and the like. The central control unit 30 executes control concerning image formation processing by the projection inversion method to be described later, in particular.

The operation unit 31 is an input device including a keyboard, various switches, a mouse, the foot pedals 31a and 31b, the touch panel 31c, and the like. The operation unit 31 is used to input patient information (a patient ID, examination region, examination purpose, and the like), vertically move the compression paddle 15, issue an imaging instruction, select a pulse rate, select an image, and input conditions concerning a scan track and the like.

The storage unit 33 stores image data or the like before or after image processing by the preprocessing unit 23. The storage unit 33 stores a dedicated program for implementing image formation processing by the projection inversion method to be described later. The storage unit 33 also stores filter coefficients (i.e., filter coefficients determined for each scan track, each image frame, and each position on an image) used in image formation processing by the projection inversion method.

(Image Formation Processing by Projection Inversion Method)

Image formation processing by the projection inversion Method (PI method) will be described next. This processing can be roughly classified into filter coefficient calculation processing and tomosynthesis image generation processing. Each processing will be described below.

[1. Tomosynthesis Image Generation Processing]

Figure 3:
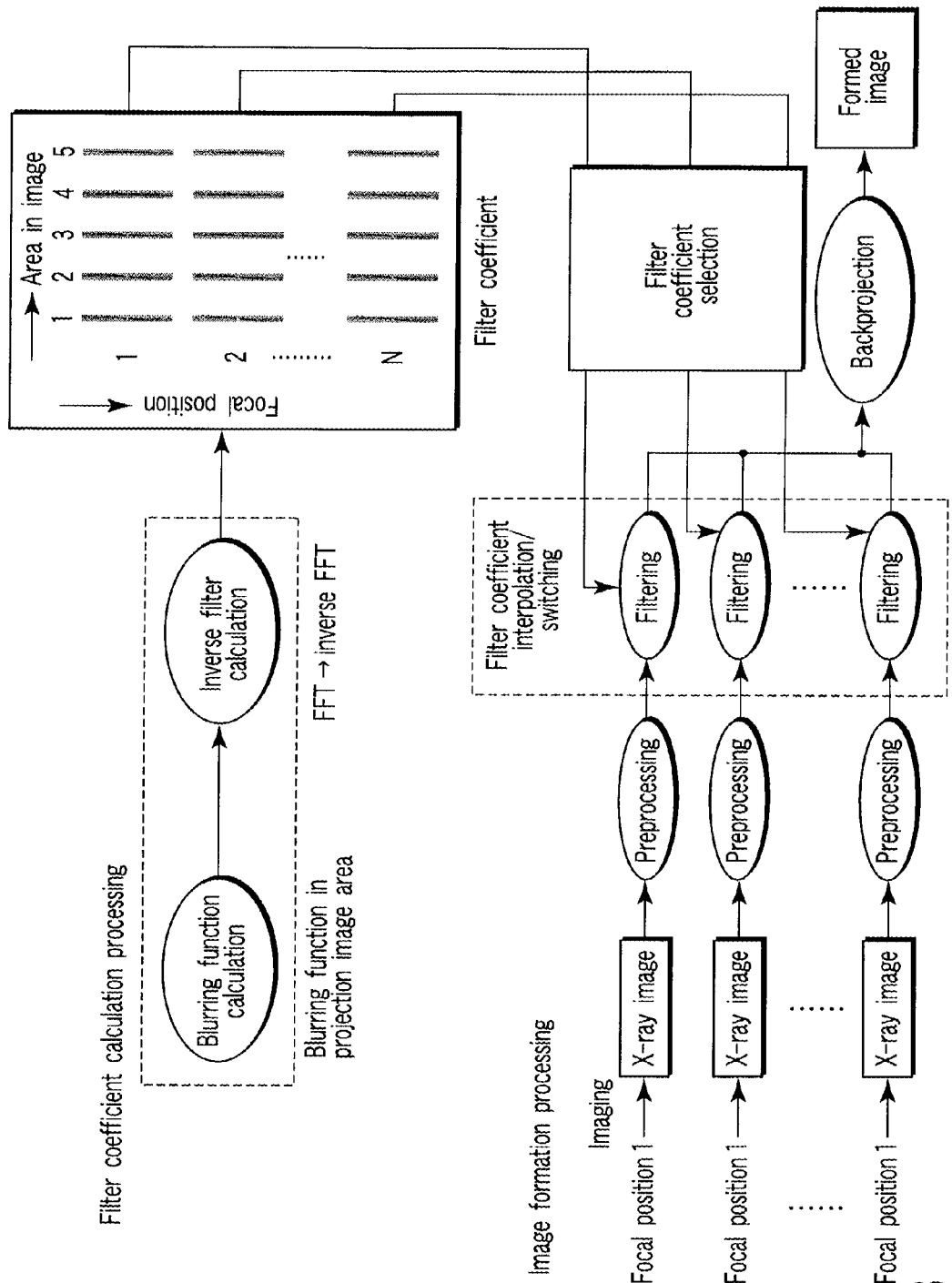
FIG. 3 is a diagram conceptually showing an image formation processing procedure by a PI method.

FIG. 3 is a diagram conceptually showing an image formation processing procedure by the PI method. As shown in FIG. 3, tomosynthesis image generation processing is the processing of obtaining a tomosynthesis image by capturing a plurality of X-ray images along a scan track and then executing preprocessing, filtering, and backprojection for the X-ray images. The filter coefficient calculated by filter coefficient calculation processing to be described later is used for filtering. Such filter coefficients differ for each scan track, each image frame, and each position on an image. Therefore, this apparatus is configured to select proper filter coefficients depending on the scan track used for imaging. The apparatus is also configured to select filter coefficients so as to apply a different filter coefficient to each of a plurality of X-ray images obtained by one imaging operation. Furthermore, since filter coefficients differ in accordance with the respective detector pixel positions of an X-ray image, the apparatus is configured to apply a different filter coefficient in accordance with each detector pixel position.

The following is the background theory of image formation processing by the PI method. Letting y be the vector form of voxel data obtained as a result of image formation processing, g be the vector form of a projection image, and Wy be the matrix form of projection computation, a projection process can be written as $$g = Wy + \epsilon \quad (1)$$

where $\epsilon$ is noise added to an X-ray image. In this case, each component of the projection image g is obtained by taking the logarithm of the ratio of X-ray dose attenuated by the absorptance distribution of the object (attenuation ratio).

According to the minimum-mean-square-error estimation method, it is known that equation (1) can be solved by equation (2) given below:

$$y^{est} = W^T \left( \frac{\sigma_\epsilon^2}{\sigma_y^2} I + WW^T \right)^{-1} g^{meas} \quad (2)$$

where $g^{meas}$ is a projection image obtained by imaging, and $\sigma_y^2$ and $\sigma_\epsilon^2$ are respectively the standard deviation of the pixel values of the respective volumes and the standard deviation of noise contained in the projection image. Here, a blurring correction projection image x defined by equation (3) is introduced:

$$x = \left( \frac{\sigma_\epsilon^2}{\sigma_y^2} I + WW^T \right)^{-1} g^{meas} \quad (3)$$

Then, equation (2) can be expressed by equation (4) given below, and the solution can be obtained by backprojection computation if x is known.

$$y^{est} = W^T x \quad (4)$$

where $W^T x$ represents that backprojection computation is performed with respect to x. According to equation (3), x is the solution of equation (5):

$$g^{meas} = \left( \frac{\sigma_\epsilon^2}{\sigma_y^2} I + WW^T \right) x \quad (5)$$

Although x can be obtained by solving the simultaneous linear equation expressed by equation (5), since this equation is a large-scale equation, the solution cannot be obtained by the direct method. It is, however, possible to obtain the solution by minimizing the objective function of equation (6) given below by using the iterative method.

$$f(X) = X^T A X - X^T g^{meas} \quad (6)$$

for $$A = \gamma^2 I + W W^T, \quad (7)$$
$$\gamma^2 = \frac{\sigma_\varepsilon^2}{\delta_y^2}, x = 2X$$

An optimization technique such as the conjugate gradient method is used to minimize equation (6). When the solution of equation (5) is to be obtained by using the conjugate gradient method, it suffices to prepare a processing routine for calculating Ax. This technique is characterized in that the above calculation can be executed without holding any large-scale matrices such as A, W, and $W^T$.

If the solution of equation (5) (the blurring correction projection image x) can be obtained by conjugate gradient method, a tomosynthesis image $y^{est}$ can be obtained by performing backprojection according to equation (4).

One of the important points of this method is that inversion is performed in a projection image area. That is, both the right- and left-hand sides of equation (5) represent images in the projection area. In contrast to this, in many other iterative solutions such as matrix inversion tomosynthesis, inversion is performed in a tomosynthesis area.

Equation (2) or equation (5) obtained by rewriting equation (2) is the equation of the optimal solution in digital tomosynthesis, and hence it is the best method to solve the equation in terms of image quality. As compared with the simple backprojection method or the filtered backprojection method, the above method can greatly improve image quality. However, the above method using the conjugate gradient method executes iterative solution several times, and hence it takes much processing time. That is, all the methods described above directly solve equation (5) to obtain the blurring correction X-ray image x. For this reason, it takes much processing time to execute this method in practice.

Considering that equation (5) is a linear equation and both the right- and left-hand sides of equation (5) represent images in the projection area, there may be filter computation for obtaining the blurring correction X-ray image x. Using filter computation makes it possible to execute processing at higher speed than the processing of solving the equation. The present inventors have derived such a filter by a certain technique (to be described later) and have confirmed the existence of filter computation which solves equation (5). The present inventors have also confirmed that an equivalent tomosynthesis image could be obtained by filter computation, and the processing time could be greatly shortened.

[2. Filter Coefficient Calculation Processing]

Filter coefficient calculation processing will be described next. In this processing, a proper filter coefficient to be applied to an X-ray image is calculated in accordance with a scan track (representing how many images are to be captured and at which focal position and detector position and in which detector direction each image is to be captured) at the time of X-ray imaging. Although this processing can be executed after X-ray imaging, the processing may be executed before X-ray imaging if a scan track for imaging is known in advance. If the number of kinds of scan tracks to be used for imaging is small, it is possible to calculate filter coefficients corresponding to the small number of scan tracks and then apply the filter coefficients calculated in advance to tomosynthesis image generation processing after imaging.

A filter coefficient differs for each scan track, and also differs for each image frame (i.e., each condition such as a focal position, detector position, or detector direction), and each pixel position in the same image (each area in the same image). Therefore, each different filter coefficient is calculated for each scan track, each image frame, and each pixel position in an image (or each detector pixel position).

Figure 4:
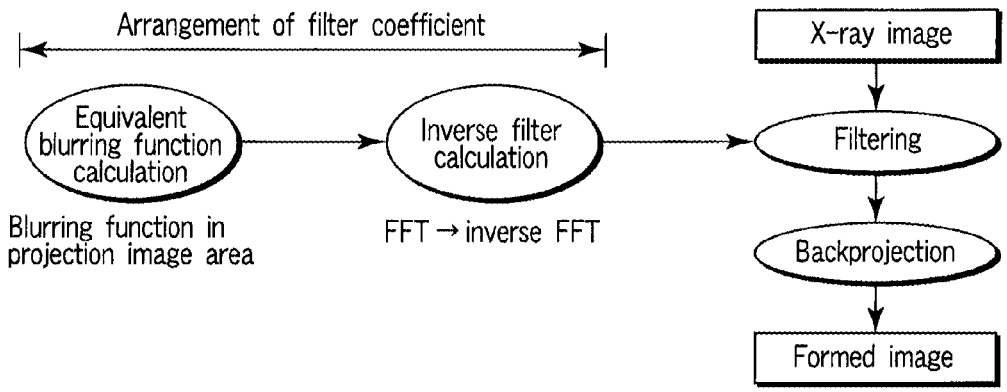
FIG. 4 is a diagram conceptually showing a calculation processing procedure for filter coefficients used in image formation processing by the PI method.
Figure 5:
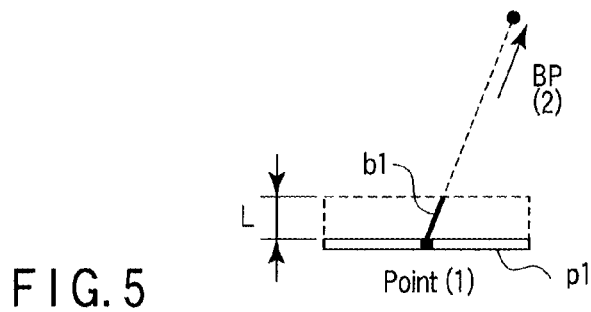
FIG. 5 is a view showing a procedure for calculating an equivalent blurring function.

FIG. 4 is a diagram conceptually showing a calculation processing procedure for filter coefficients used for image formation processing by the PI method. As shown in FIG. 4, in order to obtain a blurring correction X-ray image, this apparatus uses two steps, i.e., obtaining an equivalent blurring function $p_k$ in a projection area in advance and then forming a deconvolution filter (inverse filter calculation) with the function $p_k$ as a response function by using FFT.

[2-1. Equivalent Blurring Function Calculation Processing]

FIGS. 5 to 8 are views each showing an equivalent blurring function calculation procedure. Assume that a given detection pixel h in a given frame of a projection image is 1, and all other pixels are 0 ("(1)" in FIG. 5). Since it suffices if equivalent integration computation can be executed in subsequent processing, there is no need to generate an image set. For the sake of descriptive convenience, however, assume that an image set $p_1$ is to be generated. In addition, the apparatus obtains a backprojection image $b_1$ by performing backprojection of this image with respect to an image formation area ("(2)" in FIG. 5).

Figure 6:
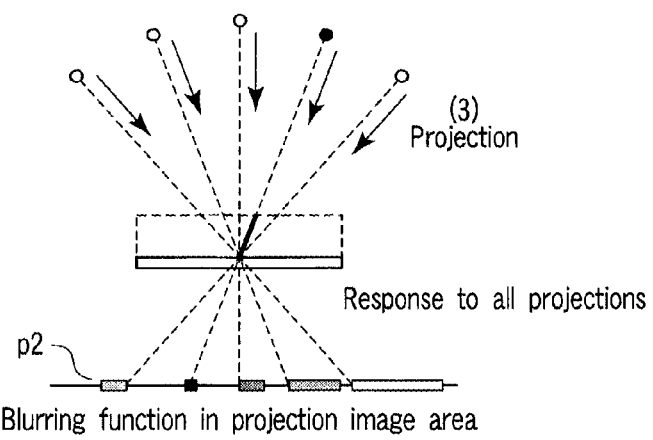
FIG. 6 is a view showing a procedure for calculating an equivalent blurring function.
Figure 7:
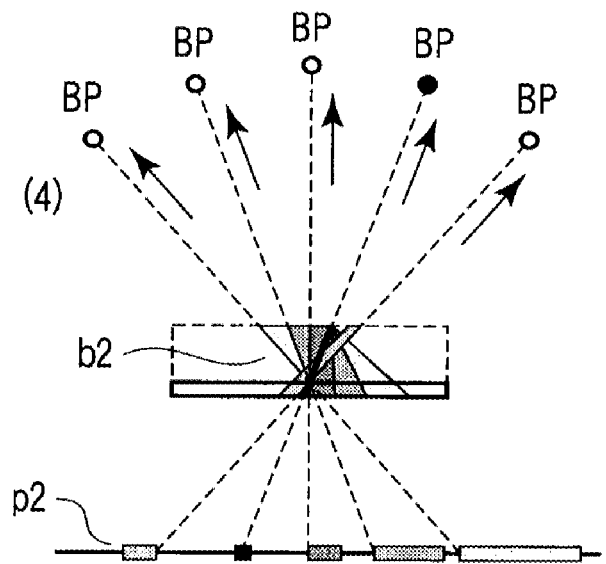
FIG. 7 is a view showing a procedure for calculating an equivalent blurring function.
Figure 8:
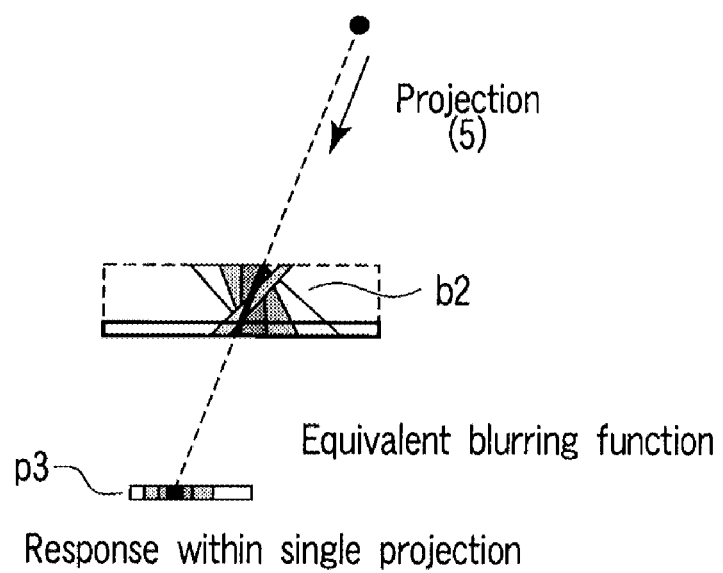
FIG. 8 is a view showing a procedure for calculating an equivalent blurring function.

The apparatus then obtains a projection image $p_2$ by projecting the backprojection image $b_1$ to all frames ("(3)" in FIG. 6). The apparatus obtains a backprojection image $b_2$ by performing backprojection of the projection image $p_2$ ("(4)" in FIG. 7). The apparatus projects the backprojection image $b_2$ to one frame in which the pixel h exists ("(5)" in FIG. 8). The equivalent blurring function $p_k$ is the one obtained by extracting an image in an image area around the pixel h from one projection image obtained by this backprojection.

Such computation of backprojection–projection–backprojection–projection can be expressed by one double integral equation. In terms of implementation, an equivalent blurring function Ph is calculated by executing this double integration.

An integral equation for the equivalent blurring function $p_h$ is obtained by executing the above process of backprojection–projection–backprojection–projection for each step. The following shows only a calculation method for this processing.

$$p_h = \frac{1}{\omega_h} \begin{pmatrix} p(d_1, d_h) \\ p(d_2, d_h) \\ \vdots \\ p(d_M, d_h) \end{pmatrix} \quad (a1)$$

$$p(d, d_h) = \int_{-L/2}^{L/2} \int_{t_1}^{t_2} \frac{V^2}{A^2} \frac{(m_k(s,t))^2}{\cos\theta_k} \frac{(m_l(s))^2}{\cos\theta_l} dt\, ds \quad (a2)$$

where $d_h$ is the coordinate value of the center of a filter, and d is a position where the value of a blurring function on the detector is to be checked. The above integration is not an equation which is not explicit function for d, and d is a variable of s and t. Numerically, however, d can be calculated by the above equation and hence it suffices to determine d within the loop of t and s and accumulate the integral on the corresponding pixel.

L is a parameter (integration area size) representing the size of an integration area, and designates the thickness of the object. Values $t_1$ and $t_2$ are obtained by using L within the integration range of t, for example, according to equations (a3) and (a4):

$$t_1 = |r - r_{sl}| + \sqrt{\frac{L^2}{4} - |r - d_h|^2},$$ (a3)

$$t_2 = |r - r_{sl}| - \sqrt{\frac{L^2}{4} - |r - d_h|^2}$$

$$r = r_{sl} - \frac{(r_k(s) - r_{sl}) \cdot (r_{sl} - d_h)}{|r_k(s) - r_{sl}|^2}(r_k(s) - r_{sl})$$ (a4)

where $r_{st}$ and $r_{sl}$ are the coordinates of focal points in projections k and l. Values $r_k(s)$ and $r_l(s, t)$ are the coordinates on projected straight lines in the projections k and l and represented by equations (a5) and (a6) by using s and t:

$$r_k(s) = \frac{(d_h - r_{sk})}{|d_h - r_{sk}|}s + d_h$$ (a5)

$$r_l(s, t) = t\frac{r_k(s) - r_{sl}}{|r_k(s) - r_{sl}|} + r_{sl}$$ (a6)

Values $m_k(s)$ and $m_l(s, t)$ are geometric magnification factor and obtained by $$m_k(s, t) = \frac{|d - r_{sk}|}{|r_l(s, t) - r_{sk}|}$$ (a7)

$$m_l(s) = \frac{|d_l(s) - r_{sl}|}{|r_k(s) - r_{sl}|}$$

Values $\theta_k$ and $\theta_l$ are angles defined by projected straight lines and the detection surface and obtained by $$\cos\theta_k = \frac{w_k^T(r_l(s, t) - r_{sk})}{|w_k||r_l(s, t) - r_{sk}|}$$ (a8)

$$\cos\theta_l = \frac{w_l^T(r_k(s) - r_{sl})}{|w_l^T||r_k(s) - r_{sl}|}$$

where $w_k$ and $w_l$ are vectors representing the normal directions of the detector in the projections k and l. A value d represents the intersection between a projected straight line connecting a focal point and $r_l(s, t)$ and the detection surface in the projection k. The intersection d can be easily calculated by using a geometric magnification factor $m_k(s, t)$ according to equation (a9):

$$d = m_k(s,t)(r_l(s,t) - r_{sk}) + r_{sk}$$ (a9)

[2-2. Inverse Filter Calculation Processing]

First of all, a vector $a_k$ is obtained. The vector $a_k$ is obtained by adding value $\gamma^2 = \sigma^2 \epsilon/\sigma^2_y$ to the equivalent blurring function $p_k$ for only a pixel corresponding to the pixel h. Note that both $a_k$ and $p_k$ represent two-dimensional images.

Letting $x_k$ be the kth frame of a blurring correction projection image x and $g_k^{meas}$ be the kth frame of a captured projection image $g^{meas}$, equation (5) is approximated by $$a_h * x_k = g_k^{meas}$$ (8)

In equation (8), since $a_k$ and $g_k^{meas}$ are known and $x_k$ is unknown, $x_k$ can be obtained by deconvolution computation. Deconvolution computation is executed by using an FFT algorithm according to equation (9) given below:

$$F[x_k] = \frac{F[g_k^{meas}]}{F[a_h]}$$ (9)

Note that F[.] represents a two-dimensional Fourier transform. In this case, an inverse filter to be obtained can be obtained by equation (10)

$$f(k, h) = F^{-1}\left[\frac{1}{F[a_h]}\right]$$ (10)

[2-3. Tomosynthesis Image Generation Processing by PI Method]

With the use of a filter coefficient f, tomosynthesis image generation processing is executed in two steps, i.e., filtering represented by equation (11) and backprojection represented by equation (4).

$$x_k = f(k,h) * g_k^{meas}$$ (11)

[2-4. Characteristics of Calculated Filter Coefficients]

Figure 9:
FIG. 9 is a view showing a case wherein a filter coefficient is calculated at a given pixel position in a given frame, and the resultant data is visualized.

FIG. 9 shows a case wherein a filter coefficient is calculated at a given pixel position in a given frame, and the resultant data is visualized. The filter coefficient calculated by such a projection inversion method has a value for each pixel position and generally has the following properties:

having a high value at a central pixel (pixel h).

having a value near 0 at a pixel far from the central pixel (pixel h).

having areas with negative values which radially extend from the central pixel (pixel h) in two opposite directions.

Figure 10:
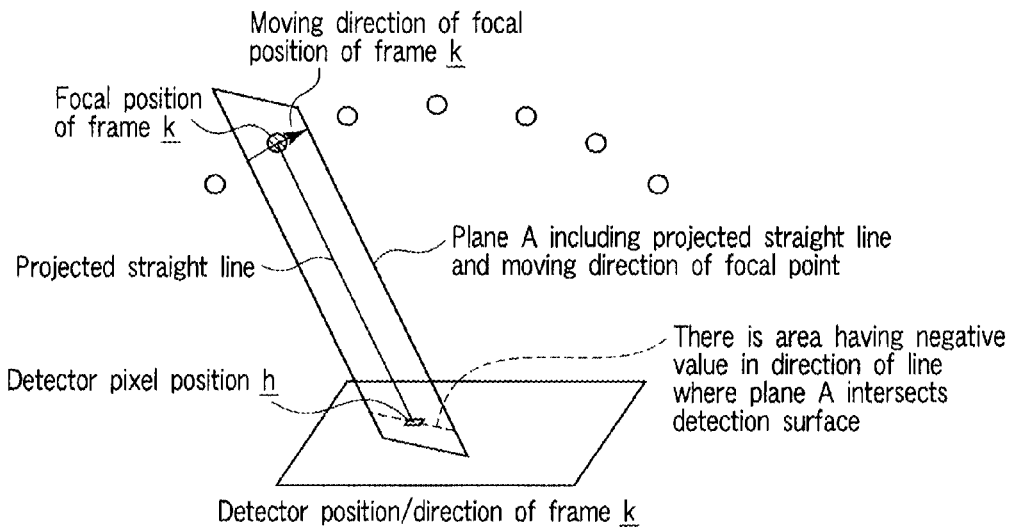
FIG. 10 is a view for explaining the characteristics of the filter coefficients calculated by the projection inversion method.

Note that the two opposite directions are the directions of a line where the detection surface intersects a plane including the projected line (the line connecting the pixel h and the focal point) and the moving direction of the focal point in FIG. 10. As shown in FIG. 10, since this method is a method of calculating an equivalent blurring function from a scan track, such a filter coefficient is obtained. In an area having a negative value, the filter coefficient has a large absolute value at a point near the central pixel and a value near 0 at a point far from the central pixel. The above properties are due to the use of the equivalent blurring function calculated by using a scan track for the calculation of the filter coefficient. With the above properties, similar image quality can be obtained regardless of the particular arrangement used for the calculation of a filter coefficient.

[2-5. Determination of Filter Coefficient in This Mammography X-Ray Diagnostic Apparatus]

A filter coefficient like that calculated by the above technique may be calculated every time a tomosynthesis image is to be generated. However, to shorten the turn around time at the time of tomosynthesis image generation, the mammography X-ray diagnostic apparatus 1 stores, in advance, filter coefficients calculated in advance (e.g., at the time of shipment of the apparatus) calculated by a computer or the like for the respective scan tracks, the respective image frames, and the respective pixel positions, and executes tomosynthesis image generation processing upon selecting a proper filter coefficient.

This apparatus selects a filter coefficient by using a filter coefficient identification character string. A filter coefficient identification character string is used to specify a scan track identification character string, a scan track calculation parameter, an image frame number, and a pixel position on an image.

A scan track identification character string is defined by a combination of the number of images to be captured (the number of frames), a scan angle (e.g., an imaging angle range when an arc scan is to be performed), a frame rate (the number of X-ray images to be captured per sec), the moving speed of the focal point/detector, and an SID (the distance between a focal point and the detector). Assume that the number of images to be capture is 41, the scan angle (the angle range in an arc scan) is 90°, the frame rate is 0.5 [frame/sec], and the SID is 900 mm. In this case, the scan track identification character string is "SP90_4frms_05dfps_sid900".

Assume that in this embodiment, a scan track identification character string is input and set by selecting conditions concerning a scan track from values preset by using an interface to be described later. However, the present invention is not limited to this, and it suffices to set a scan track identification character string by directly inputting arbitrary values or conditions.

Figure 11:
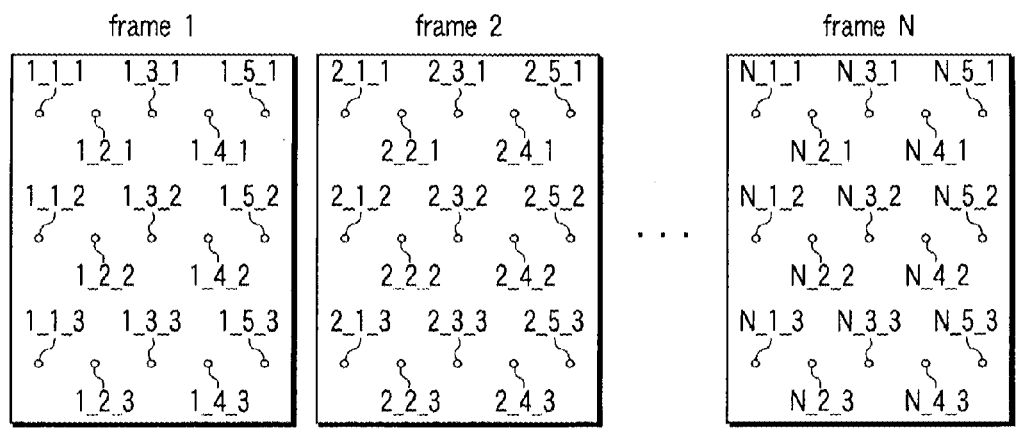
FIG. 11 is a view for explaining a technique for generating filter coefficient identification character strings.

In addition, a scan track calculation parameter includes a parameter like γ in equation (7) and a number indicating how many filter coefficient representative points are to be taken in the x and y directions. If, therefore, the scan track identification character string is "SP90_41frms_05dfps_sid900", a filter coefficient identification character string at the third place in the horizontal direction (e.g., the x direction) and the second place in the vertical direction (e.g., the y direction) in the second frame in FIG. 11 is defined as "SP90_41frms_05dfps_sid900/gamma10_n5_3/2_3_2". Note that "n5_3" in this character string represents that five points in the horizontal direction and three points in the vertical direction are used for filter calculation. Note that a filter coefficient identification character string in this embodiment is expressed by "scan track identification character string+"/"+filter coefficient calculation parameter+"/"+character string indicating detector pixel position".

The image formation processing unit 24 reads out a filter coefficient corresponding to the set filter coefficient identification character string from the storage unit 33, and stores it in correspondence with a filter coefficient identification character string in the form of file management (for example, by using the filter coefficient identification character string as part of a file name).

(Operation)

Operation in image formation processing by the PI method in the mammography X-ray diagnostic apparatus 1 will be described next.

FIG. 12 is a flowchart showing an operation procedure in image formation processing by the PI method in the mammography X-ray diagnostic apparatus 1. Referring to FIG. 12, first of all, before the execution of image formation processing, the operator inputs, with the operation unit 31, conditions concerning a scan track (i.e., conditions for determining a scan track identification character string), a scan track calculation parameter, and other image formation processing conditions (e.g., the central position of a tomosynthesis image, the size (field of view) of the tomosynthesis image, and the pixel interval of the tomosynthesis image (step S1).

Figures 13, 15:
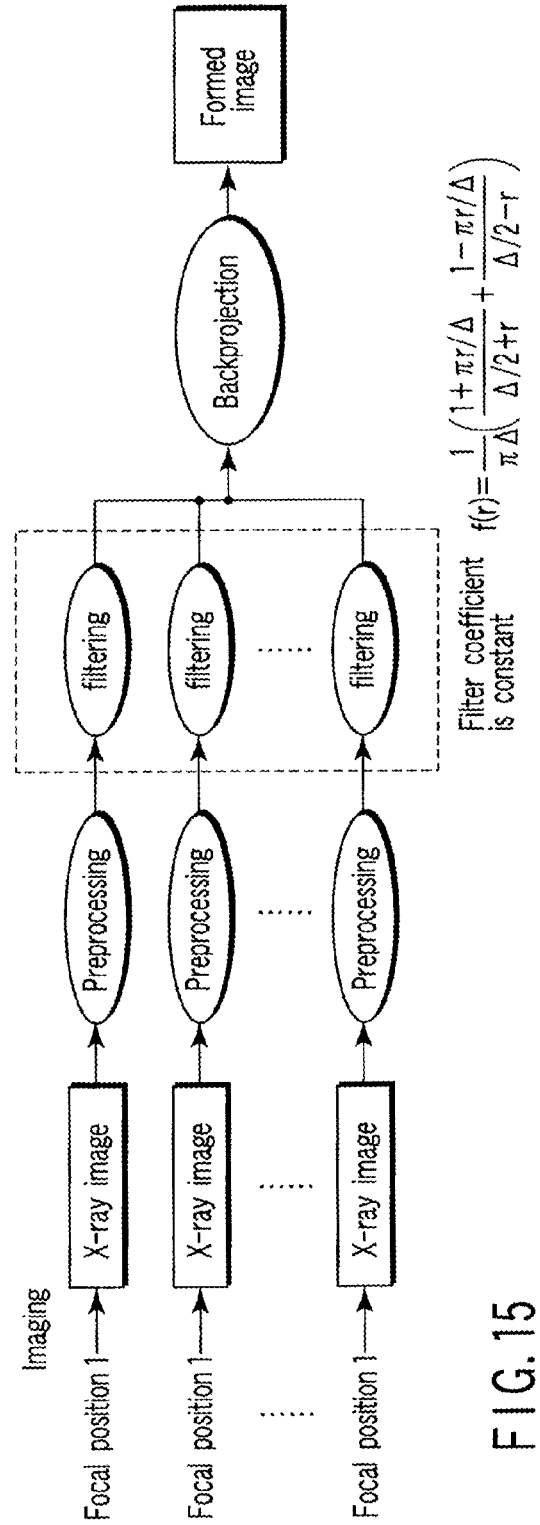
FIG. 13 is a view showing an example of an interface for inputting conditions concerning a scan track.
FIG. 15 is a view for explaining a conventional technique.

FIG. 13 is a view showing an example of an interface for inputting conditions concerning a scan track. Selecting desired values from an input window like that shown in FIG. 13 will input conditions concerning a scan track and set a corresponding scan track identification character string. In the case shown in FIG. 13 (i.e., wherein the number of images to be captured is 72, the scan angle is 30°, the frame rate is 7.2 [frame/sec], and the SID is 700 mm), the scan track identification character string is "SP90_72frms_7.2dfps_sid700".

Upon receiving an imaging start instruction from the operation unit 31, the central control unit 30 executes imaging of the designated number of X-ray images along the designated scan track and acquires a plurality of X-ray images (step S2).

The preprocessing unit 23 then executes preprocessing for the plurality of captured X-ray images (step S3). Note that this preprocessing includes offset correction, defective pixel correction processing, logarithmic computation, and the like, and pixel bundling is executed as needed.

The central control unit 30 then generates a filter coefficient identification character string for each pixel of each image (step S4). The image formation processing unit 24 executes filtering processing upon selecting filter coefficients by using the generated filter coefficient identification character strings (step S5). That is, the image formation processing unit 24 acquires a total number of representative points at which filter coefficients are calculated from the filter coefficient identification character strings and reads all filter coefficients from the file. Subsequently, the image formation processing unit 24 executes processing from (1) to (3) described below for every frame k with respect to every detector pixel (i, j).

(1) The image formation processing unit 24 determines the representative point (I, J) near the detector pixel (i, j) (i.e., calculates and determines the representative point position (I, J) from a filter coefficient identification character string).

(2) The image formation processing unit 24 specifies an associated filter coefficient by using a filter coefficient identification character string (i.e., selects an associated filter coefficient from the storage unit 33 on the basis of a filter coefficient identification character string). In this case, a filter coefficient identification character string is defined by "scan track identification character string+"/"+filter coefficient calculation parameter+"/"+"k_I_J"".

(3) The image formation processing unit 24 executes filtering by using a filter coefficient associated with the frame k and the detector pixel (i, j).

A tomosynthesis image is generated by executing backprojection processing using the image having undergone the filtering processing (step S6). This backprojection processing is executed on the basis of the scan track specified by the scan track identification character string and other designated image formation processing conditions. The display unit 27 displays the generated tomosynthesis image, which is automatically stored in the storage unit 33 (step S7).

The above technique is an example of using a filter coefficient at a representative point nearest each pixel of the detector. However, a method of determining a filter coefficient by interpolation is also available. For example, four representative points near the pixel (i, j) of the detector are selected. In this case, four representative points are selected such that the pixel (i, j) is included in a rectangle formed by the four representative points. A filter coefficient at the pixel (i, j) is obtained from filter coefficients at the four representative points by bilinear interpolation. In the case of bilinear interpolation, four representative points are selected. When another interpolation method is used, the number of representative points to be selected differs.

Figure 14:
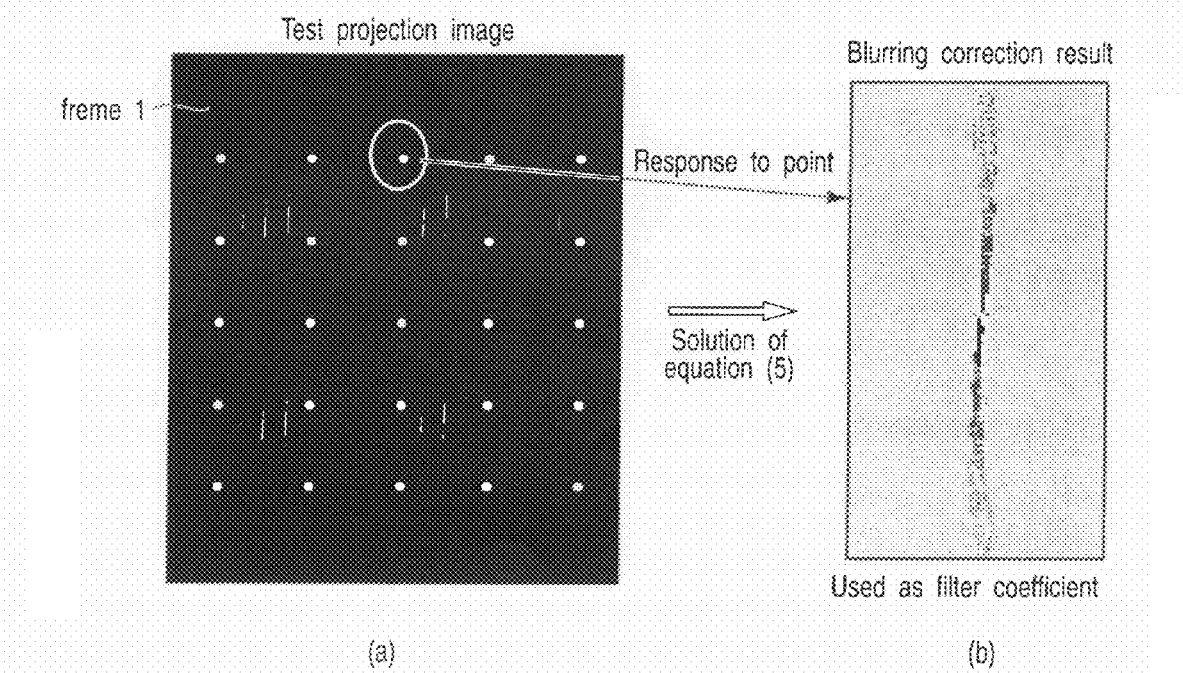
FIG. 14 is a view for explaining a filter coefficient extraction method.

In filter coefficient calculation processing, filter coefficients can also be obtained by a filter coefficient extraction method instead of the above technique (direct construction method). Filter coefficient calculation processing using this technique is performed as follows. First of all, a pseudo projection image is generated. This projected image is generated on the assumption that a point and a strip exist in an image formation area (FIG. 14(a)). The projected images of points are arranged in a grid pattern, and the projected images of strips are inserted between the projected images of the points. Assume that the direction of each strip coincides with the direction in which a strip is projected as a point with respect to one of all the 11 projection images. The solution x of equation (5) is obtained by the iterative solution method using equation (6) based on this projection image or another method. As a result, a response to the point projected image is obtained (FIG. 14(b)). The filter coefficient extraction method is a method of extracting this response as a filter coefficient. Filtering the projection image by using the obtained filter coefficient and executing backprojection can execute processing equivalent to the iterative method given by equation (6) at high speed.

According to the above arrangement, the following effects can be obtained.

This X-ray diagnostic apparatus applies preprocessing to each image obtained by capturing a plurality of X-ray images at a plurality of X-ray tube positions and then performs filtering processing and backprojection, thereby generating a tomosynthesis image. At this time, the apparatus determines proper filter coefficients used for filtering for the respective scan track, the respective image frames, and the respective pixel positions in an image. This determination of a filter coefficient corresponds to obtaining the equation of the optimal solution (see equations (2) and (5)) in the digital tomosynthesis method by filter computation. This technique can therefore generate a tomosynthesis image with higher image quality than that generated by the conventional technique, and can contribute to an improvement in the quality of diagnosis.

This X-ray diagnostic apparatus need not perform iterative computation processing in tomosynthesis image generation, and selects a filter coefficient for each pixel position from filter coefficients calculated and stored in advance by using a filter coefficient identification character string. Therefore, the apparatus need not calculate any filter coefficient from the beginning every time a tomosynthesis image is to be generated. The apparatus can therefore shorten the turn around time from imaging operation to tomosynthesis image display while acquiring a tomosynthesis image with high image quality.

Note that the present invention is not limited to the above embodiments, and constituent elements can be variously modified and embodied at the execution stage within the spirit and scope of the invention. For example, the following are concrete modifications.

Each function associated with each embodiment can also be implemented by installing programs for executing the corresponding processing in a computer such as a workstation and mapping them in a memory. In this case, the programs which can cause the computer to execute the corresponding techniques can be distributed by being stored in recording media such as magnetic disks (floppy® disks, hard disks, and the like), optical disks (CD-ROMs, DVDs, and the like), and semiconductor memories.

In addition, various inventions can be formed by proper combinations of a plurality of constituent elements disclosed in the above embodiments. For example, several constituent elements may be omitted from all the constituent elements disclosed in the above embodiments. Furthermore, constituent elements in the different embodiments may be properly combined.

What is claimed is:

1. An image processing apparatus comprising:
a storage unit which stores X-ray images for a plurality of frames which are acquired by applying X-rays to a subject to be examined while an X-ray tube is moved along a predetermined scan track and a different filter coefficient for each scan track, each frame of each X-ray image, and each pixel position of a detector;
a filter processing unit which determines filter coefficients for each X-ray image on the basis of combinations of the predetermined scan track of each X-ray image, the frame of each X-ray image, and the pixel position of the detector, and executes filter processing for the X-ray images or processed images thereof for the plurality of frames by using the determined filter coefficients; and
a tomosynthesis image generating unit which generates a tomosynthesis image by using the X-ray images for the plurality of frames after filter processing.

2. An apparatus according to claim 1, further comprising an input unit for inputting the predetermined scan track.

3. An apparatus according to claim 1, wherein the filter coefficients stored in the storage unit are determined for each combination of a scan track, a respective of the plurality of frames of the X-ray images, a pixel position of the detector by calculating an equivalent blurring function as a two-dimensional image for each combination of a scan track, a respective of the plurality of frames of the X-ray images, and a pixel position of the detector, calculating a deconvolution function of the equivalent blurring function, and using the deconvolution function.

4. An apparatus according to claim 1, wherein the filter unit uses interpolation processing for the filter coefficients.

5. An apparatus according to claim 1, wherein each filter coefficient has a high value at a central pixel and a value near 0 at a pixel far from the central pixel, and areas having negative values radially extend in opposite two directions determined with reference to the central pixel.

6. An apparatus according to claim 5, wherein the two opposite directions are directions of a line where a plane including a projected straight line and a moving direction of a focal point intersects a detection surface.

7. An apparatus according to claim 5, wherein in the area having the negative value, each filter coefficient has a large absolute value at a point near the central pixel and a value near 0 at a point far from the central pixel.

8. An X-ray diagnostic apparatus comprising:
an imaging unit which applies X-rays to a subject to be examined while moving an X-ray tube along a predetermined scan track, and detects X-rays which enter a detection surface of a detector;
an image generating unit which generates X-ray images for a plurality of frames on the basis of the detected X-rays;
a storage unit which stores a different filter coefficient for each scan track, each frame of an X-ray image, and each pixel position of the detector;
a filter processing unit which determines filter coefficients for each X-ray image on the basis of combinations of the predetermined scan track of each X-ray image, the frame of each X-ray image, and the pixel position of the detector, and executes filter processing for the X-ray images or processed images thereof for the plurality of frames by using the determined filter coefficients; and
a tomosynthesis image generating unit which generates a tomosynthesis image by using the X-ray images for the plurality of frames after filter processing.

9. An apparatus according to claim 8, further comprising an input unit for inputting the predetermined scan track.

10. An apparatus according to claim 8, wherein the filter coefficients stored in the storage unit are determined for each combination of a scan track, a respective of the plurality of frames of the X-ray images, a pixel position of the detector by calculating an equivalent blurring function as a two-dimensional image for each combination of a scan track, a respective of the plurality of frames of the X-ray images, and a pixel position of the detector, calculating a deconvolution function of the equivalent blurring function, and using the deconvolution function.

11. An apparatus according to claim 8, wherein the filter unit uses interpolation processing for the filter coefficients.

12. An apparatus according to claim 9, wherein each filter coefficient has a high value at a central pixel and a value near 0 at a pixel far from the central pixel, and areas having negative values radially extend in opposite two directions determined with reference to the central pixel.

13. An apparatus according to claim 12, wherein the two opposite directions are directions of a line where a plane including a projected straight line and a moving direction of a focal point intersects a detection surface.

14. An apparatus according to claim 12, wherein in the area having the negative value, each filter coefficient has a large absolute value at a point near the central pixel and a value near 0 at a point far from the central pixel.

15. A method of calculating a filter coefficient used for reconstruction processing in digital tomosynthesis in an X-ray diagnostic apparatus, the method causing a computer to calculate an equivalent blurring function as a two-dimensional image for each combination of each scan track, each frame of an X-ray image, and each pixel position of the detector, calculate a deconvolution function of the equivalent blurring function, and calculate a filter coefficient for each combination of a scan track, a frame of an X-ray image, and a pixel position of the detector by using the deconvolution function.

16. A method according to claim 15, further comprising storing the calculated filter coefficient in association with scan start information.

17. A method of calculating a filter coefficient used for reconstruction processing in digital tomosynthesis in an X-ray diagnostic apparatus, the method causing a computer to calculate an equivalent blurring function by executing double integral with respect to backprojection, projection, backprojection, and projection, calculate a deconvolution function of the equivalent blurring function, and calculate a filter coefficient for each combination of a scan track, a frame of an X-ray image, and a pixel position on each X-ray image by using the deconvolution function.

18. A method according to claim 17, further comprising storing the calculated filter coefficient in association with scan start information.

* * * * *